United States Patent [19]

Kuracina et al.

[11] Patent Number: 4,998,922
[45] Date of Patent: Mar. 12, 1991

[54] SAFETY SYRINGE CAP MINIMIZING NEEDLE-STICK PROBABILITY

[76] Inventors: Thomas C. Kuracina, 15974 Maricopa Hwy., Ojai, Calif. 93023; Randall Ohnemus, 6292 Bell St., Ventura, Calif. 93003

[21] Appl. No.: 484,915

[22] Filed: Feb. 23, 1990

[51] Int. Cl.⁵ .............................................. A61M 5/32
[52] U.S. Cl. ................................... 604/192; 604/263
[58] Field of Search ................. 604/192, 187, 198, 263

[56] References Cited

U.S. PATENT DOCUMENTS

| | | | |
|---|---|---|---|
| 3,134,380 | 5/1964 | Armao | 604/6198 |
| 4,139,009 | 2/1979 | Alvarez | 604/198 |
| 4,790,828 | 12/1988 | Dombrowski et al. | 604/198 |
| 4,867,172 | 9/1989 | Haber et al. | 604/198 X |

*Primary Examiner*—John D. Yasko
*Attorney, Agent, or Firm*—Donald A. Streck

[57] ABSTRACT

This invention is a lockable and retractable safety cap for covering the needle of a hypodermic syringe to prevent accidental needle-stick. There is a unitary cap assembly of a resiliently flexible plastic material including a hub portion disposed concentrically about a base portion of the needle and attached to the barrel, a sliding safety hub portion having a bore therethrough slidably disposed with the needle passing through the bore and extending over a point end of the needle, and a plurality of slats extending between the hub portion and the sliding safety hub portion. The slats are parallel to the needle whereby a longitudinal compressive force against the sliding safety hub portion is resisted by a longitudinal compressive resistance of the slats which must be overcome before the slats will deform and flex outward from the needle to expose the needle for use. A releasable safety latch assembly can be disposed over the slats for preventing deforming and outward flexing thereof. The preferred assembly comprises a coil spring disposed over the slats, a sliding collar carried by an outer end of the coil spring, a retaining button located on one of the slats adjacent the inner end for holding the sliding collar to retain the coil spring in a compressed state, and a release for releasing a hold on the sliding collar when the slats bends outward whereby following use of the syringe the coil spring is released and returns to an extended state.

17 Claims, 4 Drawing Sheets

SAFETY SYRINGE CAP MINIMIZING NEEDLE-STICK PROBABILITY

BACKGROUND OF THE INVENTION

This invention relates to safety covers for the needle of a hypodermic syringe and, more particularly, in a hypodermic syringe having a barrel with a needle extending outward therefrom, to a retractable safety cap for covering the needle to prevent accidental needle-stick therefrom comprising a unitary cap assembly of a resiliently flexible plastic material including a hub portion disposed concentrically about a base portion of the needle and attached to the barrel, a sliding safety hub portion having a bore therethrough slidably disposed with the needle passing through the bore and extending over a point end of the needle, and a plurality of slats extending between the hub portion and the sliding safety hub portion, the slats being spaced from one another along adjacent edges thereof at radially equal intervals about the periphery of the needle and being parallel to the needle whereby a longitudinal compressive force against the sliding safety hub portion is resisted by a longitudinal compressive resistance of the slats which must be overcome before the slats will deform and flex outward from the needle to allow the sliding safety hub portion to slide along and expose the needle for use.

So-called "needle-stick" is a major problem among health workers such as doctors, nurses, and the like. Needle-stick is the accidental puncturing of the skin of a health worker while working with hypodermic syringes. Needle-stick, per se, is not a new phenomenon for health care workers. In the past, however, it was more of an inconvenience than anything else. The present level of activity of serum-transmitted diseases such as hepatitis and AIDS, however, has transformed needle-stick from a mere inconvenience to a major consideration for health care workers. When a health care worker is stuck, he or she must be tested for exposure to the various serum-transmitted diseases such as hepatitis and AIDS. Even if such diseases were never actually contracted from the invasion of the needle through the skin, the costs of such testing would be (and are) considerable. Unfortunately, the diseases are contracted by such accidental needle-stick. Thus, the health care worker who is stuck must suffer the mental anguish of possibly having contracted hepatitis or AIDS by virtue of the accident.

Figures 1, 2, 3, 4, 5:
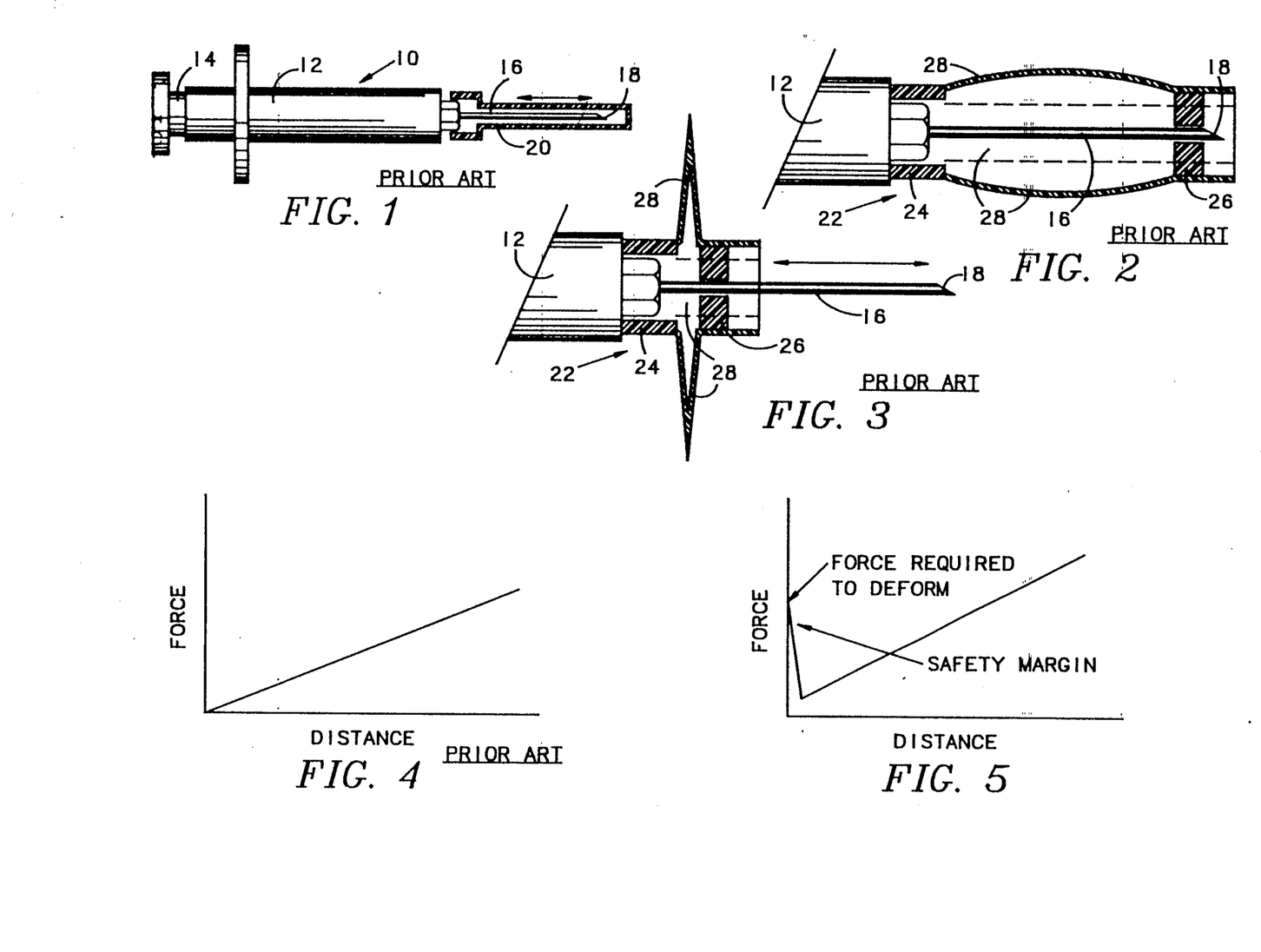
FIG. 1 is a simplified partially cutaway drawing of a hypodermic syringe showing a prior art removeable needle cap.
FIG. 2 is a simplified partially cutaway drawing of the needle portion of a hypodermic syringe showing a prior art needle protective sheath with retracts to expose the needle with the sheath in its extended position.
FIG. 3 is a simplified partially cutaway drawing of the needle portion of a hypodermic syringe of FIG. 2 showing the prior art needle protective sheath with the sheath in its retracted position.
FIG. 4 is a graph depicting the force required to retract the prior art needle protective sheath of FIGS. 2 and 3.
FIG. 5 is a graph depicting the force required to retract the needle protective sheath of the present inventin in its simplest embodiment.

The typical syringe in use today is as depicted in FIG. 1 where it is generally indicated as 10. The syringe 10 has a cylindrical barrel 12 into which a cylindrical plunger 14 is slidable inserted at one end. A needle 16 is attached to the opposite end of the barrel 12. For ease of puncturing the skin of a patient, the end of the needle 16 terminates in an extremely sharp chisel point 18. The needle 16 is covered with a removeable cylindrical cap 20 which typically lockingly attaches to the barrel 12. To remove the needle cap 20 for use of the syringe 10, the cap 20 is rotated to unlock it from the barrel 12 and then removed from over the needle 16. Once the protective cap 20 is removed, the point 18 is exposed and available for unintended needle-stick. For example, the syringe 10 could be dropped and stick into the user or anyone in the area at any point of the body in the path of descent. The cap 20 is also replaced on the syringe 10 after use for safety purposes. That process itself is a major contributor to needle-stick as it is easy for the user to miss the opening to the cap 20 with the needle 16 and stick a finger which is holding the cap 20.

Needle-stick is not a problem which has gone un-noticed in the art. Unfortunately, with one exception which will be addressed shortly, those persons inventing with an eye to preventing needle-stick have not done so in a realistic manner. Typically, what is offered as a solution is a complicated hypodermic syringe construction which (while it may work to prevent needle-stick) is so complex as to drive the cost of a syringe beyond that which the health care industry is willing to pay. For example, one popular prior art approach is to have the needle 16 be mounted for automatic retraction into the barrel 12 after use. As can be appreciated, not only is such construction complex and, therefore, extremely expensive; but, it does not take into consideration how such parts can be produced. As can be appreciated, the cylindrical barrel 12 and plunger 14 of the prior art syringe 10 of FIG. 1 are easily and inexpensively produced employing injection molding techniques with plastic. The syringes come pre-sterilized in a plastic wrap and are discarded after a single use thereby minimizing the costs associated with each single injection.

The single known exception to the general and complete impracticality of prior art approaches to preventing needle-stick is that suggested by Dr. Marcial Alvarez in his 1979 U.S. Pat. No. 4,139,009. This is not to say that Dr. Alvarez's retractable needle cap is a complete solution to the problem. There are, in fact, problems with Dr. Alvarez's approach which account for the fact that despite the extreme nature of the problem and the fact that Dr. Alvarez's design has been available to the art for over eleven years, the Alvarez solution has not been adopted by the suppliers of syringes. What the Alvarez cap suggests, however, is that there can be a simple and inexpensive approach to solving the needle-stick problem employing standard disposable syringes. The Alvarez approach is depicted in greatly simplified form in FIGS. 2 and 3 wherein his retractable cap is generally indicated as 22. The cap 22 comprises a cylindrical hub 24 which attaches to the barrel 12 of the syringe 10 in the same manner as the prior art cap 20. An annular slider member 26 fits over the needle 16 adjacent the point 18. A plurality (four being suggested) of bowed members 28 (four being suggested) extend from the hub 24 to the slider member 26 and extend out over the point 18 of the needle 16 so as to completely encase the needle 16. In use, the slider member 26 can be pressed against the rubber cover of a bottle (to fill the syringe 10) or against the skin of a patient (to inject from the syringe 10). By pushing the syringe forward, the slider member 26 is urged backward along the needle 16 as the bowed members 28 bow outward to a retracted position as in FIG. 3. Alternately, the slider member 26 can be gripped and retracted as, for example, when doing an intravenous injection in which the positioning of the needle 16 must be observed.

On paper and as a first impression, the Alvarez apparatus appears to be an ideal solution to the needle-stick problem. When one contemplates the totality of its operation and investigates the practicalities of producing it on a commercial level, however, certain shortcoming become apparent. For one thing, it is virtually impossible to mold the retractable cap 22 of Alvarez. Moreover, if one counts the parts in the retractable cap 22 of Alvarez as depicted in the patent drawings, there are five parts to each cap. As those skilled in the art are readily aware, each part of a device adds to the cost of manufacture and assembly. When manually retracting the cap 22 of Alvarez by gripping the slider member 26, it can be seen and appreciated that it would be an easy matter to have a finger in the line of movement of the needle point 18 and be stuck by it. Moreover, with the cap 22 in its "safety" position of FIG. 2, if one were to longitudinally bump the slider member 26, it is highly likely that the slider member 26 would retract sufficiently to allow the point 18 of the needle 16 to stick someone sufficiently to puncture the skin. This can be seen with reference to the graph of FIG. 4. As soon as some longitudinal force is applied to the slider member 26 of the Alvarez cap 22, the slider member 26 begins to move back and expose the point 18 of the needle 16. What would be desirable would be a retractable cap which would perform as depicted in FIG. 5; that is, have a step force which must be overcome before the cap begins to retract. The step force should be sufficient to prevent retraction from normal bumping force. Even more ideal would be a way of locking the cap from retraction until actual retraction was desired.

Two approaches somewhat similar to Alvarez are contained in the 1988 patents to Hagen (U.S. Pat. No. 4,735,618) and Dombrowski et al. (U.S. Pat. No. 4,790,828).

Wherefore, it is an object of the present invention to provide a retractable safety cap for covering the needle of a hypodermic syringe to minimize the opportunity of needle-stick which is simple and inexpensive to manufacture.

It is another object of the present invention to provide a retractable safety cap for covering the needle of a hypodermic syringe to minimize the opportunity of needle-stick which is reliable in operation.

It is yet another object of the present invention to provide a retractable safety cap for covering the needle of a hypodermic syringe to minimize the opportunity of needle-stick which can be employed with prior art syringes without any necessity of modifying the syringe.

It is still another object of the present invention to provide a retractable safety cap for covering the needle of a hypodermic syringe to minimize the opportunity of needle-stick which has a safety threshold of force necessary to retract the cap which will avoid retraction from normal longitudinal bumping forces.

It is a still further object of the present invention to provide a retractable safety cap for covering the needle of a hypodermic syringe to minimize the opportunity of needle-stick which has a safety lock associated therewith which will avoid retraction until desired.

Other objects and benefits of the invention will become apparent from the detailed description which follows hereinafter when taken in conjunction with the drawing figures which accompany it.

SUMMARY

The foregoing objects have been achieved in a hypodermic syringe having a barrel with a needle extending outward therefrom by the lockable and retractable safety cap for covering the needle to prevent accidental needle-stick therefrom of the present invention comprising a unitary cap assembly of a resiliently flexible plastic material includiing a hub portion disposed concentrically about a base portion of the needle and attached to the barrel, a sliding safety hub portion having a bore therethrough slidably disposed with the needle passing through the bore and extending over a point end of the needle, and a plurality of slats extending between the hub portion and the sliding safety hub portion, the slats being spaced from one another along adjacent edges thereof at radially equal intervals about the periphery of the needle and being parallel to the needle whereby a longitudinal compressive force against the sliding safety hub portion is resisted by a longitudinal compressive resistance of the slats which must be overcome before the slats will deform and flex outward from the needle to allow the sliding safety hub portion to slide along and expose the needle for use; and, a releasable safety latch disposed over the slats for preventing deforming and outward flexing thereof whereby the cap assembly is locked and resistance to accidental needle-stick is increased when the syringe is not in use.

In the preferred embodiment, the releasable safety latch comprises a coil spring disposed over the slats so as to be compressible adjacent an inner end of the slats at the hub portion to allow the slats to deform and flex outward. Additionally, there is a sliding collar carried by an outer end of the coil spring opposite the inner end of the slats.

The preferred embodiment also includes retaining button means located on one of the slats adjacent the inner end for holding the sliding collar to retain the coil spring in a compressed state adjacent the inner end of the slats. The preferred retaining button means includes release means for releasing a hold on the sliding collar when the one of the slats bends outward whereby when the one of the slats returns to an unbent state following use of the syringe the coil spring is released and returns to an extended state from a self-bias force thereof.

Preferably, the retaining button means includes a button for preventing the sliding collar from sliding along the slats; and, the release means comprises, a tab on the one of the slats facing the hub portion and carrying the retaining button, and a strongback formed along an inner surface of the one of the slats disposed between a midpoint of the one of the slats and a point adjacent a rear edge of the tab whereby as the one of the slats bends outward the strongback pivots the tab downward about the rear edge thereby lowering the button an amount sufficient for the sliding collar to slide thereover.

DESCRIPTION OF THE PREFERRED EMBODIMENT

Figures 6, 7, 8:
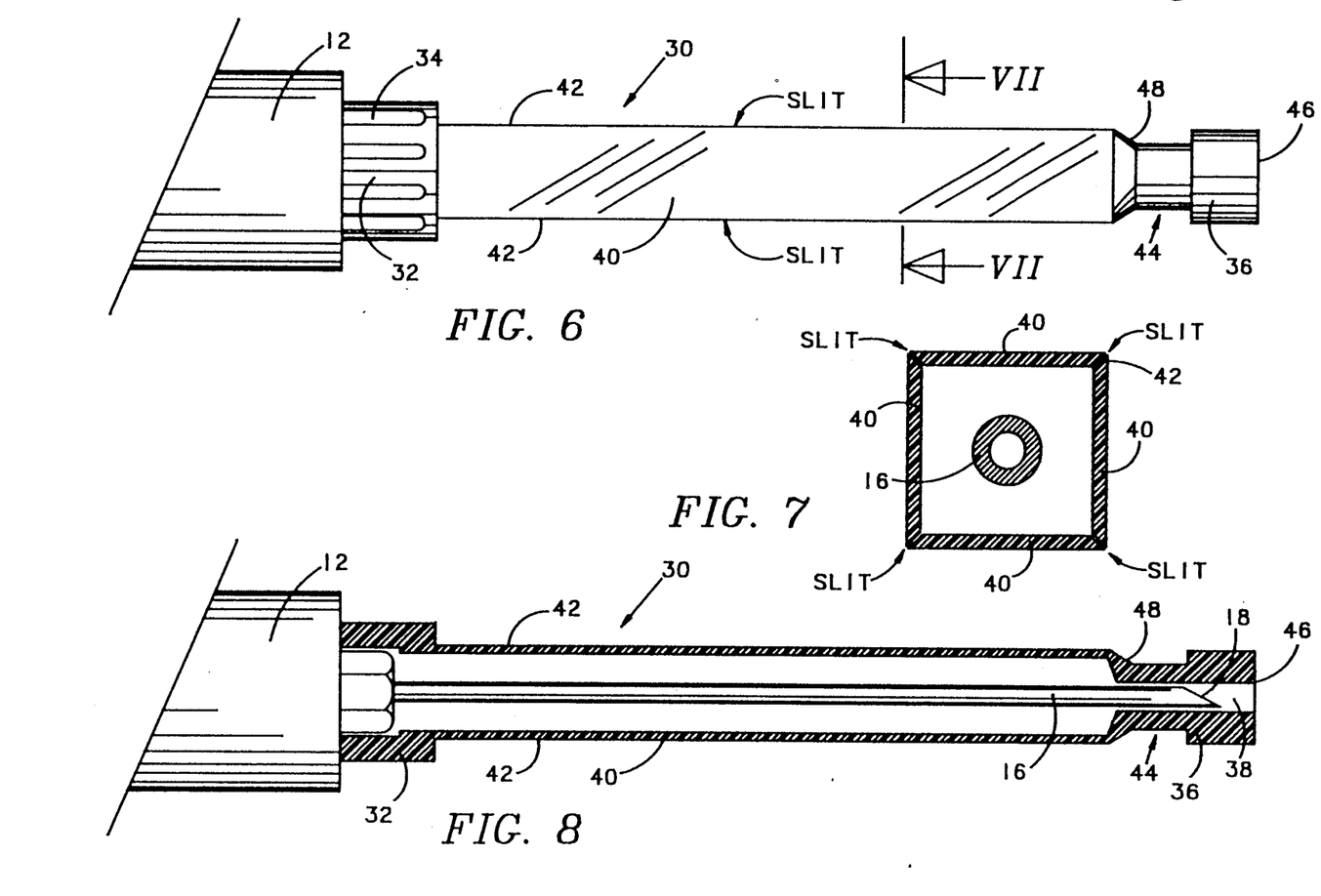
FIG. 6 is a simplified side view drawing of the needle portion of a hypodermic syringe showing the needle protective sheath of the present invention in its simplest embodiment.
FIG. 7 is a cutaway end view drawing of the protective sheath of the present invention at plane VII—VII of FIG. 6 depicting the preferred square cross section.
FIG. 8 is a simplified partially cutaway side view drawing of the needle portion of a hypodermic syringe showing the needle protective sheath of the present invention of FIG. 6.
Figures 9, 10, 11:
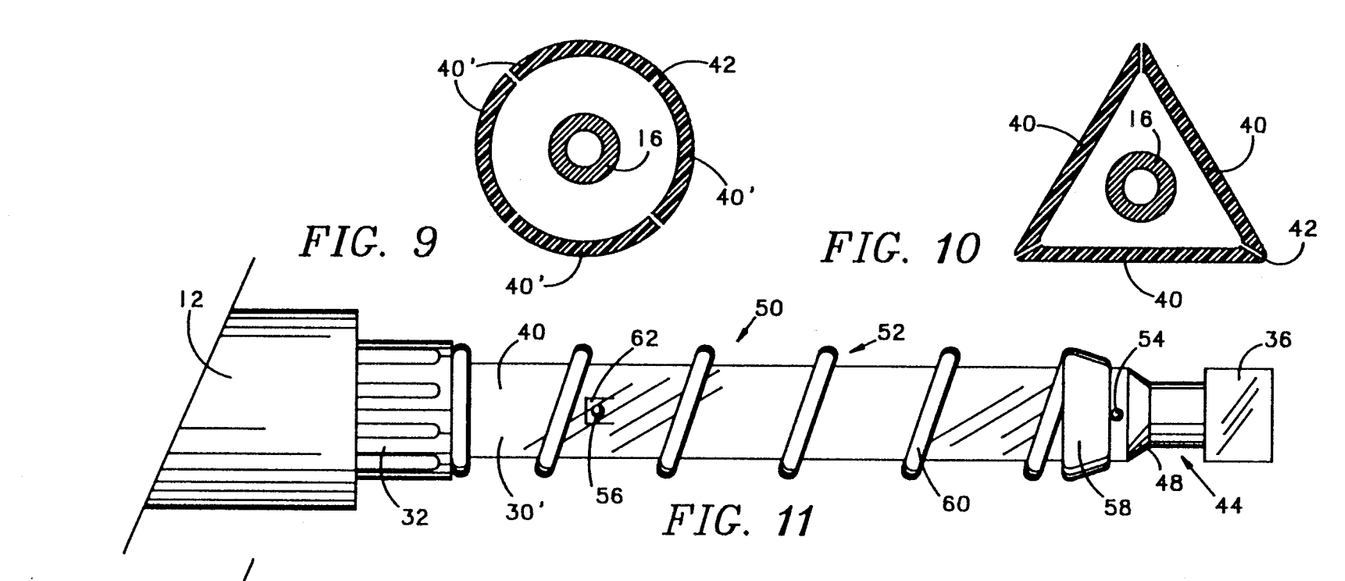
FIG. 9 is a cutaway end view drawing of the protective sheath of the present invention depicting an alternate embodiment which has a circular cross section.
FIG. 10 is a cutaway end view drawing of the protective sheath of the present invention depicting another alternate embodiment which has a triangular cross section.
FIG. 11 is a simplified side view drawing of the needle portion of a hypodermic syringe showing the needle protective sheath of the present invention in its preferred embodiment incorporating a locking spring over the sheath.

The retractable safety cap of the present invention is shown in its most basic preferred form in FIGS. 6-8 where it is generally indicated as 30. The cap 30 is of a molded plastic such as polypropylene and, as indicated in FIG. 8, is of unitary construction. As those skilled in the molding art will appreciate, the design is such as to be easily and inexpensively molded. Since there is only one part, there is no cost of assemble associated with the cap 30. The cap 30 comprises a cylindrical hub portion 32 which is adapted to lockingly engage the barrel 12 of a standard syringe 10. The hub portion 32 has grooves 34 formed into the exterior surface so as to enhance the gripping thereof when mounting the cap 30 onto the barrel 12 of the syringe 10. Ridges could, of course, be substituted for the grooves 34 if desired and both could be eliminated with affecting the novel aspects of the cap 30. The opposite end of the cap 30 is formed as a sliding safety hub 36. The hub 36 has a longitudinal bore 38 therethrough which slides on the needle 16. The hub 36 also extends out over the point 18 of the needle 16. In the preferred embodiment, the hub portion 32 and sliding safety hub 36 are interconnected by four flat slats 40 disposed at 90° interval around the needle 16 so as to form a square box around the needle 16 as shown in FIG. 7. Note that the slats 40 abut one another along their longitudinal edges in slits 42 so as to be free to move independently. Note also that the slats 40 are not bowed with respect to the needle 16; that is, they are parallel thereto along the entire length from the hub portion 32 to the sliding safety hub 36. The sliding safety hub 36 has a circumferential groove 44 disposed back from the outer end 46. The bottom edge 48 of the groove 44 is angled as depicted. This provides two functions. For one, the groove 44 can be gripped to manually retract the cap 30 without danger of the user's fingers being in the line of movement of the needle point 18. For another, the angle of the edge 48 provides a slight outward force on the slats 40 to assure that they move outward for full retractability rather than moving inward against the needle, which would prevent full retractability. One may also wish to make the material of the cap 30 where the slats 40 join the sliding safety hub 36 slightly thinner so that bending will take place at that point. The angle of the edge 48 makes that an easy task. In passing, it should be noted that the sliding safety hub 36 could be square if desired; but, a cylindrical shape is more esthetically pleasing and, therefore, in the preferred embodiment the sliding safety hub 36 is generally cylindrical and smoothly curves to a square cross section where it joins the slats 40. If desired, the slats could be formed as cylindrical segments 40' as depicted in FIG. 9 or, in the alternative, more or fewer flat slats 40 could be employed as in the triangular cross section of FIG. 10. Moreover, it is also preferred that the surface of the outer end 46 have a roughened texture formed therein so as to grip the skin of a patient and thereby minimize any possibility of slipping.

It is the foregoing construction which causes the safety cap 30 of this invention to perform in the manner shown in the graph of FIG. 5. Since the slats 40 are parallel to the needle 16, an initial longitudinal force against the outer end 46 is wholly a compressive force along the length of the slats 40. Thus, as depicted in the graph of FIG. 5, the force must increase to a level where the slats suddenly begin to deform outward. Once this threshold level is overcome, a lower bending resistive force is all that is imparted by the slats 40. It is contemplated that using polypropylene for the slats 40 a thickness of 10 mils will afford the proper initial resistance and subsequent restorative force; that is, once the cap 30 has been retracted, it should reliably, quickly, and positively return to its protective position covering the needle 16 as the needle 16 is withdrawn from the patient. Initial prototype testing was done using a cylindrical arrangment as depicted in FIG. 9. Since a cylindrical segment is more resistive to longitudinal compressive forces than a flat slat, satisfactory performance was achieved with a 4 mil wall thickness. It is on this basis that 10 mils is projected as being optimum for the flat slats of the preferred embodiment.

Turning now to FIG. 11 through 16 where it is generally indicated as 50, the safety cap of the present invention in its preferred embodiment incorporating a safety latch will now described in detail. As those skilled in the art will readily note and appreciate, the preferred safety cap 50 is comprised of only two components—the basic safety cap 30' (slightly modified) and a spring latch 52. The basic safety cap 30' is substantially as described above with the addition of an outer retention button 54 and an inner retention button 56 on the slats 40. The buttons 54, 56 will be addressed in greater detail shortly.

Figure 12:
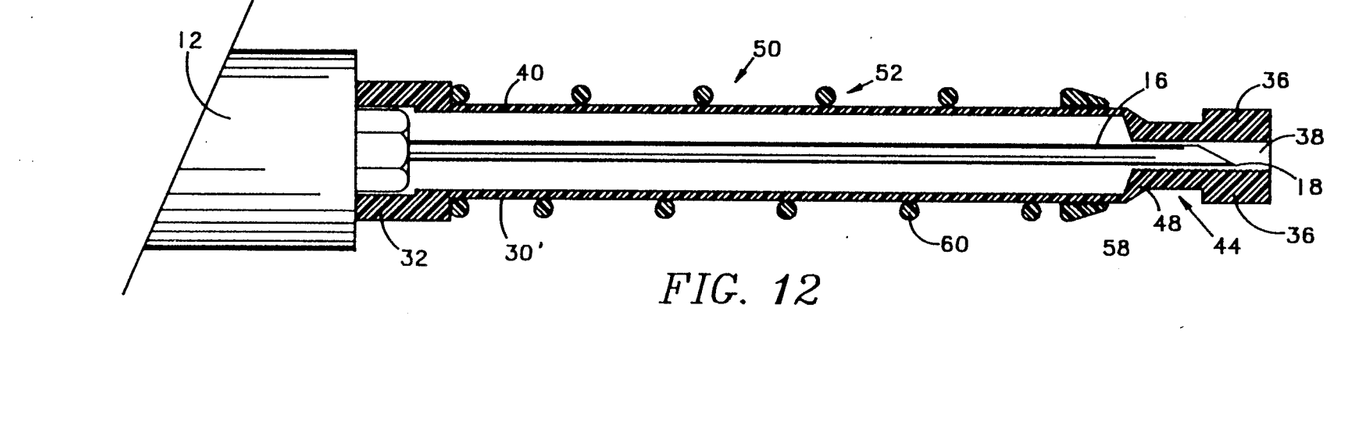
FIG. 12 is a cutaway side view drawing of the protective sheath and locking spring of FIG. 11.

The spring latch 52 is of unitary construction and comprises a sliding collar 58 formed on one end of a coil spring 60. The collar 58 and spring 60 are sized and shaped to fit close to the surface of the slats 40 yet slide surely and easily therealong between an extended (i.e. locked) position as depicted in FIGS. 11 and 12 and a retracted (i.e. unlocked) position as depicted in FIG. 13 and 14.

The spring latch 52 is slid over the slats 40 of the basic cap 30' and held in place by the outer retention button 54. For assembly purposes of this embodiment, it may be preferable to make the sliding safety hub portion 36 of square cross section. In passing it should also be noted that one button 54 could be employed; but, that two buttons 54 disposed on opposite sides 180° C. from one another are preferred. As will be appreciated, with the spring latch 52 in its extended and locked position of FIGS. 11 and 12, it is virtually impossible to cause the slats 40 to bow outward. Thus, longitudinal compressive resistance continues to meet and resist any longitudinal force attempting to expose the point 18 of the needle 16 and needle-stick is virtually eliminated. Of course, if the syringe were to be projected in the manner of a dart under extremely high force, something might give resulting in exposure of the point 18. Under normally-encountered forces, however, needle-stick should not occur.

Figure 13:
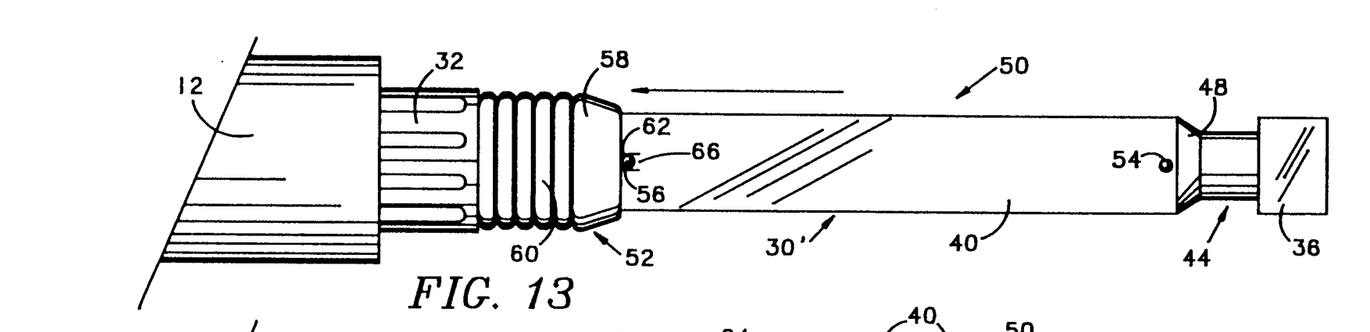
FIG. 13 is a simplified side view drawing of the needle protective sheath of the present invention in its preferred embodiment of FIG. 11 with the locking spring withdrawn to a latched position which allows the sheath to be retracted.
Figures 14, 15, 16:
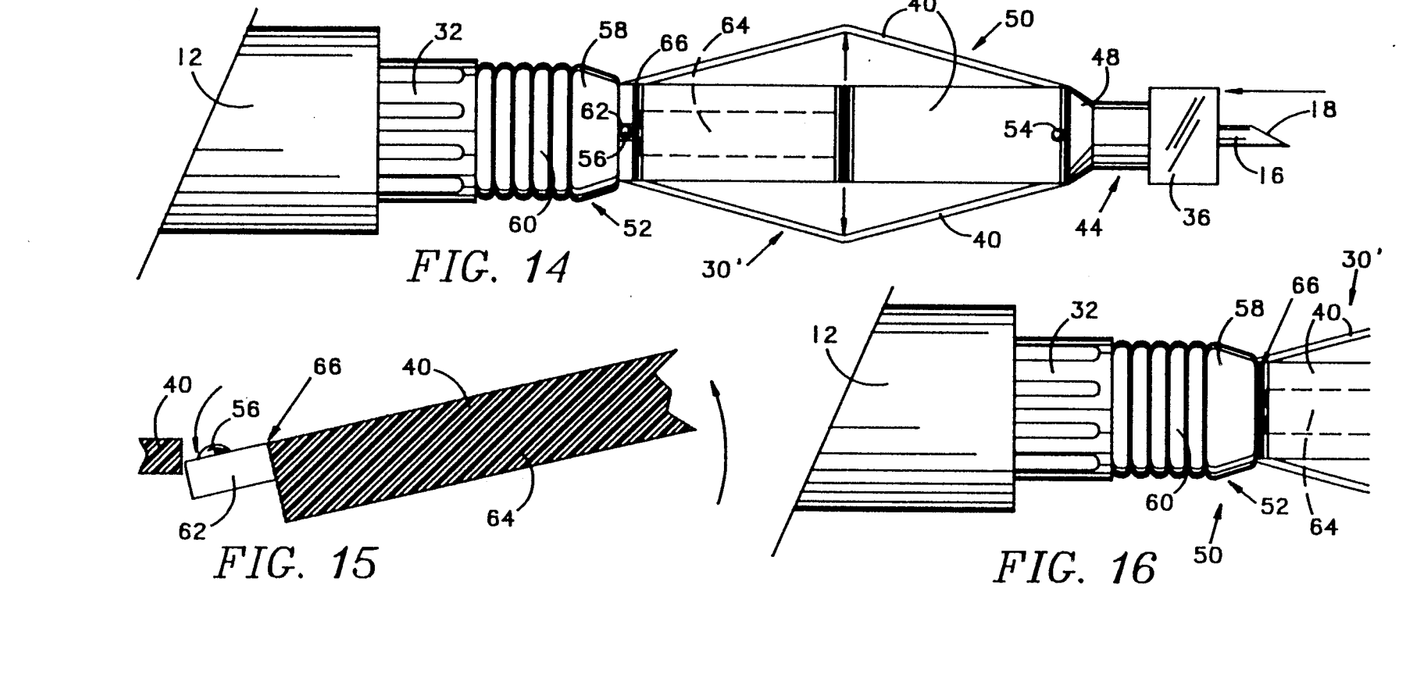
FIG. 14 is a simplified side view drawing of the needle protective sheath of the present invention in its preferred embodiment of FIGS. 11 and 13 with the locking spring withdrawn to its latched position and the sheath in the process of being retracted.
FIG. 15 is a simplified enlarged drawing of the latching button at the base of the sheath depicting the way in which the button releases the spring during retraction of the sheath.
FIG. 16 is a simplified side view drawing of the needle protective sheath of the present invention with the locking spring released from its latched position so as to automatically return to its locked position when the sheath is released from its retracted position.

To use the syringe 10, the pring latch 52 is retracted to the position of FIG. 13 by gripping the sliding collar 58 and sliding it towards the hub portion 32 where it is held by the inner retention button 56. As with the outer retention button 54 as discussed above, one button 56 could be used but two spaced on opposite sides at 180° intervals is preferred. With the coil spring 60 withdrawn from its extended position surrounding the slats 40, the sliding safety hub 36 can be slid along the needle 16 to expose it for use in the manner described above with respect to the basic cap 30 and as depicted in FIG. 14.

The inner retention button 56 is included in the preferred embodiment to make use of a syringe 10 including the safety cap 50 as easy as possible. The inner retention button 56 could, of course, be eliminated if desired without making use of the syringe 10 excessively difficult. It should be noted at this point that just as the material and thickness of the slats 40 is chosen so that the slats 40 will flex when the sliding safety hub 36 is retracted but retain their plastic "memory" and therefore urge the sliding safety hub 36 back to its extended position, the coil spring 60 portion of the spring latch 52 is also of a material and thickness so as to have a sufficient spring constant which will return the spring latch 52 to its extended position of FIG. 11 when it is released. If the inner retention button 56 is employed to hold the spring latch 52 in its retracted position, those skilled in the art will recognize and appreciate that provision must be made to repeatedly and positively release the sliding collar 58 so as to allow the spring latch 52 to automatically return to its locked safety position and maximize the protection afforded by the cap 50 against accidental needle-stick following use of the syringe 10. Such provision is included in the cap 50 and will now be described.

The inner retention button 56 is mounted on a tab 62 formed into the slat 40. The tab 62 faces towards the syring 10. Additionally, as shown ghosted in FIG. 14 and in side view in FIG. 15, a strongback 64 is formed into the slat 40 containing the inner retention button 56 between a point adjacent the midpoint of the slat 40 and the back edge 66 of the tab 62. As will best be understood with reference to FIG. 15, when the sliding collar 58 has been slid over the inner retention button 56 and is being held thereby and the sliding safety hub portion 36 is slid towards the syringe 10 to expose the needle 16, the slats 40 begin to deform outward in the manner depicted in FIG. 14. In so doing, the strongback 64 is raised and pivots about the back edge 66 of the tab 62 since it is the weakest point adjacent the rear of the slat 40 containing the tab 62. The portions of the slat 40 on opposite side of the tab 62 bend; however, the tab 62 being free to move moves downward pivoting about its back edge 66 as depicted in FIG. 15. As the tab 62 pivots about its back edge 66, the inner retention button 56 moved downward sufficiently to release the sliding collar 58. The sliding collar 58 then moves forward under its self-biasing force over the button 56 to the position of FIG. 16 where it is held from extending by the outwardly bent slats 40. As will be recognized and appreciated by those skilled in the art by this point, when the inward compressive force on the sliding safety hub portion 36 is released and the slats 40 return to their flatted and extended position, the sliding collar 58 is no longer held and prevented from allowing the spring latch 52 to extend and, therefore, it immediately and automatically extends to lock the cap 50.

Thus, it will be appreciated by those skilled in the art from the foregoing description and the accompanying drawings that the present invention has truly met its state objectives by providing a retractable safety cap for attachment to a standard syringe as a replacement for the rigid needle cap of the standard syringe to thereby provide an inexpensive and positive means of protecting health care workers and others against accidental needle-stick to the maximum degree possible.

Wherefore, having thus described the present invention, what is claimed is:

1. In a hypodermic syringe having a barrel with a needle extending outward therefrom, a retractable safety cap for covering the needle to prevent accidental needle-stick therefrom comprising a unitary cap assembly of a resiliently flexible plastic material including:
   (a) a hub portion disposed concentrically about a base portion of the needle and attached to the barrel;
   (b) a sliding safety hub portion having a bore therethrough slidably disposed with the needle passing through said bore and extending over a point end of the needle; and,
   (c) a plurality of slats extending between said hub portion and said sliding safety hub portion, said slats being spaced from one another along adjacent edges thereof at radially equal intervals about the periphery of the needle and being parallel to the needle whereby a longitudinal compressive force against said sliding safety hub portion is resisted by a longitudinal compressive resistance of said slats which must be overcome before said slats will deform and flex outward from the needle to allow said sliding safety hub portion to slide along and expose the needle for use.

2. The retractable safety cap for a hypodermic syringe of claim 1 wherein:
   there are four said slats wherein said slats are flat so that the safety cap is square in cross section along the length of said slats.

3. The retractable safety cap for a hypodermic syringe of claim 1 wherein:

there are four said slats wherein said slats are semicylindrical so that the safety cap is cylindrical in cross section along the length of said slats.

4. The retractable safety cap for a hypodermic syringe of claim 1 and additionally comprising:
releaseable safety latch means disposed over said slats for preventing deforming and outward flexing thereof whereby resistance to accidental needle-stick is increased when the syringe is not in use.

5. The retractable safety cap for a hypodermic syringe of claim 4 wherein said releaseable safety latch means comprises:
a coil spring disposed over said slats so as to be compressible adjacent an inner end of said slats at said hub portion to allow said slats to deform and flex outward.

6. The retractable safety cap for a hypodermic syringe of claim 5 and additionally comprising:
a sliding collar carried by an outer end of said coil spring opposite said inner end of said slats.

7. The retractable safety cap for a hypodermic syringe of claim 6 and additionally comprising:
retaining button means located on one of said slats adjacent said inner end for holding said sliding collar to retain said coil spring in a compressed state adjacent said inner end of said slats.

8. The retractable safety cap for a hypodermic syringe of claim 7 wherein:
said retaining button means includes release means for releasing a hold on said sliding collar when said one of said slats bends outward whereby when said one of said slats returns to an unbend state following use of the syringe said coil spring is released and retrns to an extended state from a self-bias force thereof.

9. The retractable safety cap for a hyprodermic syringe of claim 8 wherein:
(a) said retaining button means includes a button for preventing said sliding collar from sliding along said slats; and,
(b) said release means comprises,
(b1) a tab on said one of said slats facing said hub portion and carrying said retaining button, and
(b2) a strongback along an inner surface of said one of said slats disposed between a midpoint of said one of said slats and a point adjacent a rear edge of said tab whereby as said one of said slats bends outward said strongback pivots said tab downward about said rear edge thereby lowering said button an amount sufficient for said sliding collar to slide thereover.

10. In a hypodermic syringe having a barrel with a needle extending outward therefrom, a lockable and retractable safety cap for covering the needle to prevent accidental needle-stick therefrom comprising:
(a) a unitary cap assembly of a resiliently flexible plastic material including,
(a1) a hub portion disposed concentrically about a base portion of the needle and attached to the barrel,
(a2) a sliding safety hub portion having a bore therethrough slidably disposed with the needle passing through said bore and extending over a point end of the needle, and
(a3) a plurality of slats extending between said hub portion and said sliding safety hub portion, said slats being spaced from one another along adjacent edges thereof at radially equal intervals about the periphery of the needle and being parallel to the needle whereby a longitudinal compressive force against said sliding safety hub portion is resisted by a longitudinal compressive resistance of said slats which must be overcome before said slats will deform and flex outward from the needle to allow said sliding safety hub portion to slide along and expose the needle for use; and,
(b) releaseable safety latch means disposed over said slats for sliding movement between a retracted position where said slats can deform and flex outward and an extended safety position where deforming and outward flexing of said slats is prevented, said releaseable safety latch means including bias means for biasing said releaseable safety latch means towards said extended safety position whereby said cap assembly is automatically locked and resistance to accidental needle-stick is increased when the syringe is not in use.

11. The lockable and retractable safety cap for a hypodermic syringe of claim 10 wherein said releaseable safety latch means comprises:
a coil spring disposed over said slats so as to be compressible adjacent an inner end of said slats at said hub portion to allow said slats to deform and flex outward.

12. The lockable and retractable safety cap for a hypodermic syringe of claim 11 and additionally comprising:
a sliding collar carried by an outer end of said coil spring opposite said inner end of said slats.

13. The lockable and retractable safety cap for a hypodermic syringe of claim 12 and additionally comprising:
retaining button means located on one of said slats adjacent said inner end for holding said sliding collar to retain said coil spring in a compressed state adjacent said inner end of said slats.

14. The lockable and retractable safety cap for a hypodermic syringe of claim 13 wherein:
said retaining button means includes release means for releasing a hold on said sliding collar when said one of said slats bends outward whereby when said one of said slats returns to an unbent state following use of the syringe said coil spring is released and returns to an extended state from a self-bias force thereof.

15. The lockable and retractable safety cap for a hypodermic syringe of claim 14 wherein:
(a) said retaining button means includes a button for preventing said sliding collar from sliding along said slats; and,
(b) said release means comprises,
(b1) a tab on said one of said slats facing said hub portion and carrying said retaining button, and
(b2) a strongback along an inner surface of said one of said slats disposed between a midpoint of said one of said slats and point adjacent a rear edge of said tab whereby as said one of said slats bends outward said strongback pivots said tab downward about said rear edge thereby lowering said button an amount sufficient for said sliding collar to slide thereover.

16. A lockable and retractable safety cap for covering a needle of a hypodermic syringe having a barrel with the needle extending outward therefrom to prevent accidental needle-stick comprising:

(a) a unitary cap assembly of a resiliently flexible plastic material including a hub portion disposed concentrically about a base portion of the needle and attached to the barrel, a sliding safety hub portion having a bore therethrough slidably disposed with the needle passing through said bore and extending over a point end of the needle, and a plurality of slats extending between said hub portion and said sliding safety hub portion, said slats being spaced from one another along adjacent edges thereof at radially equal intervals about the periphery of the needle and being parallel to the needle whereby a longitudinal compressive force against said sliding safety hub portion is resisted by a longitudinal compressive resistance of said slats which must be overcome before said slats will deform and flex outward from the needle to allow said sliding safety hub portion to slide along and expose the needle for use;

(b) releaseable safety latch means disposed over said slats for preventing deforming and outward flexing thereof, said releaseable safety latch means comprising, (b1) a coil spring disposed over said slats so as to be compressible adjacent an inner end of said slats at said hub portion to allow said slats to deform and flex outward, (b2) a sliding collar carried by an outer end of said coil spring opposite said inner end of said slats, (b3) retaining button means located on one of said slats adjacent said inner end for holding said sliding collar to retain said coil spring in a compressed state adjacent said inner end of said slats, and (b4) release means for releasing a hold on said sliding collar when said one of said slats bends outward whereby when said one of said slats returns to an unbent state following use of the syringe said coil spring is released and returns to an extended state from a self-bias force thereof.

17. The lockable and retractable safety cap for a hypodermic syringe of claim 16 wherein:

(a) said retaining button means includes a button for preventing said sliding collar from sliding along said slats; and, (b) said release means comprises, (b1) a tab on said one of said slats facing said hub portion and carring said retaining button, and (b2) a strongback along an inner surface of said one of said slats disposed between a midpoint of said one of said slats and a point adjacent a rear edge of said tab whereby as said one of said slats bends outward said strongback pivots said tab downward about said rear edge thereby lowering said button an amount sufficient for said sliding collar to slide thereover.

* * * * *